(12) United States Patent
Morikawa et al.

(10) Patent No.: US 10,203,308 B2
(45) Date of Patent: Feb. 12, 2019

(54) SAMPLE CONCENTRATION DEVICE

(71) Applicant: SHIMADZU CORPORATION, Kyoto-shi, Kyoto (JP)

(72) Inventors: Tsuyoshi Morikawa, Kyoto (JP); Kohji Okada, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 14/760,254

(22) PCT Filed: Jan. 15, 2014

(86) PCT No.: PCT/JP2014/050585
§ 371 (c)(1),
(2) Date: Jul. 10, 2015

(87) PCT Pub. No.: WO2014/112527
PCT Pub. Date: Jul. 24, 2014

(65) Prior Publication Data
US 2015/0346166 A1 Dec. 3, 2015

(30) Foreign Application Priority Data

Jan. 18, 2013 (JP) .................................. 2013-007079

(51) Int. Cl.
*G01N 30/24* (2006.01)
*G01N 30/84* (2006.01)
(Continued)

(52) U.S. Cl.
CPC ............. *G01N 30/24* (2013.01); *G01N 30/84* (2013.01); *G01N 30/7233* (2013.01); *G01N 2030/027* (2013.01); *G01N 2033/0019* (2013.01)

(58) Field of Classification Search
CPC .......................... G01N 30/24; G01N 2030/027
See application file for complete search history.

(56) References Cited

U.S. PATENT DOCUMENTS 4,840,730 A * 6/1989 Saxena .............. B01D 15/1807
210/103
9,177,772 B1 * 11/2015 Wiederin .............. H01J 49/105
(Continued)

FOREIGN PATENT DOCUMENTS

JP 6-273403 A 9/1994
JP 3476417 B2 12/2003
(Continued)

OTHER PUBLICATIONS

International Search Report dated Apr. 8, 2014, issued in corresponding application No. PCT/JP2014/050585 (2 pages).
(Continued)

*Primary Examiner* — David M. Gray
*Assistant Examiner* — Andrew V Do
(74) *Attorney, Agent, or Firm* — Westerman, Hattori, Daniels & Adrian, LLP

(57) ABSTRACT

A controller for controlling the operations of an autosampler, a sample push unit, and a make-up unit includes a pump stop timing setting unit for setting a first timing T1 of completion of dilution of a sample, and a subsequent second timing T2 of completion of trapping of a sample in the trap column, a dilution control unit for causing a solvent delivery pump for make-up of the make-up unit to operate, and for stopping operation of the solvent delivery pump for make-up at the first timing T1 set by the pump stop timing setting unit, and a sample push control unit for causing a solvent delivery pump for sample push of the sample push unit to operate, and for stopping operation of the solvent delivery pump for sample push at the second timing T2 set by the pump stop timing setting unit.

8 Claims, 7 Drawing Sheets

(51) Int. Cl.
    *G01N 30/02*     (2006.01)
    *G01N 33/00*     (2006.01)
    *G01N 30/72*     (2006.01)

(56) References Cited

U.S. PATENT DOCUMENTS

| | | |
|---|---|---|
| 2002/0011437 A1 | 1/2002 | Kaito et al. |
| 2012/0024048 A1 | 2/2012 | Maeda |

FOREIGN PATENT DOCUMENTS

| | | |
|---|---|---|
| JP | 3109378 U | 5/2005 |
| JP | 2005-257575 A | 9/2005 |
| JP | 2006-292641 A | 10/2006 |
| JP | 2006-343271 A | 12/2006 |
| WO | 2010/119801 A1 | 10/2010 |

OTHER PUBLICATIONS

Office Action dated Oct. 28, 2016, issued in counterpart Chinese Application No. 201480003912.2, with English tanslation. (8 pages).
Office Action dated Oct. 1, 2018, issued in counterpart Indian Application No. 4504/CHENP/2015 (5 pages).

\* cited by examiner

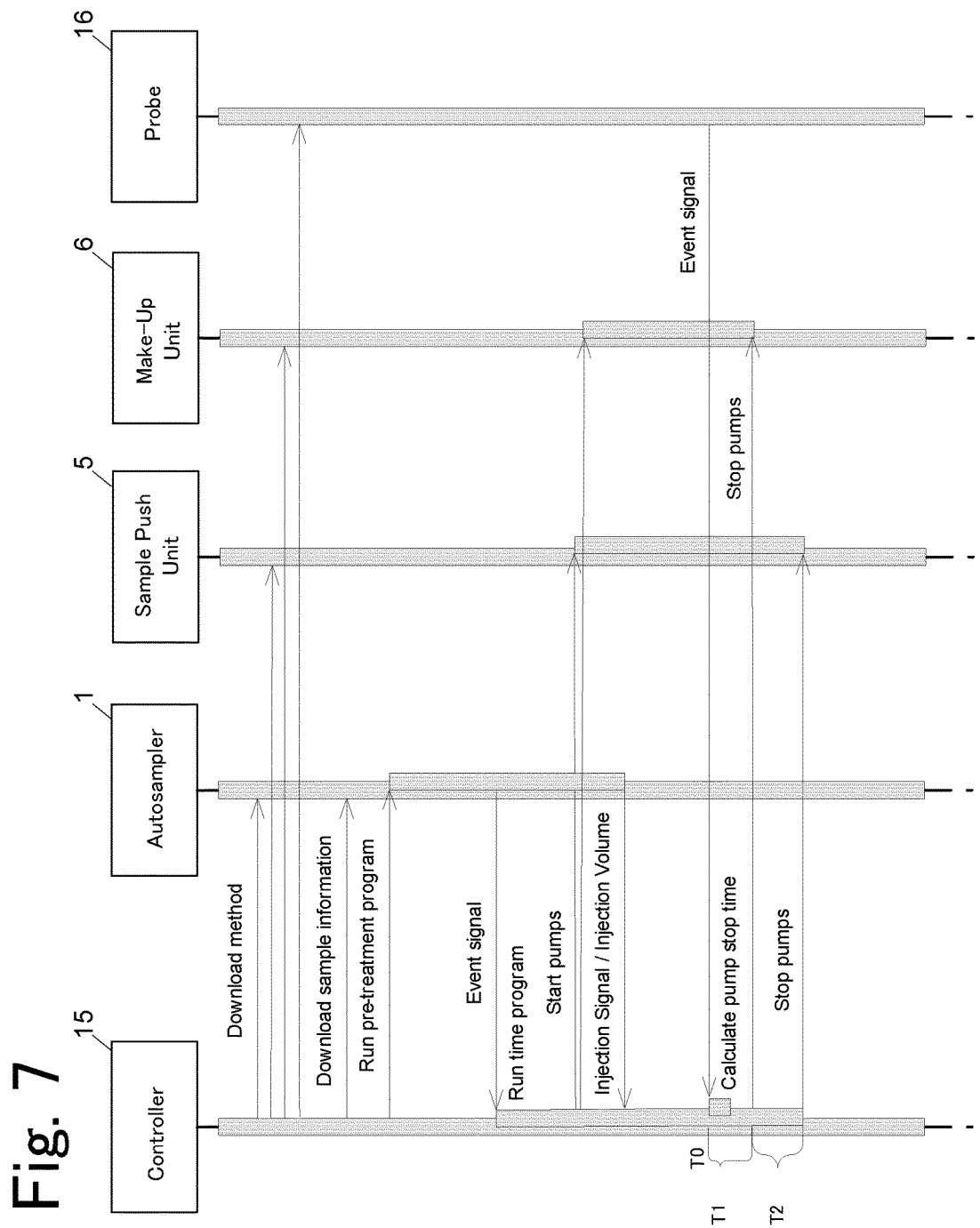

SAMPLE CONCENTRATION DEVICE

TECHNICAL FIELD

The present invention relates to a sample concentration device based on a trap column, and, for example, may be used as a device for performing a concentration process on the fractions of a sample obtained by fractionation by a preparative LC (liquid chromatograph) or as a device for performing, at an LCMS (liquid chromatograph—mass spectrometry), a concentration process on the fractions of a sample separated by an LC and supplied to an MS as a sample.

BACKGROUND ART

As a method of extracting synthesized compounds as a single component, generally, a method of using a preparative liquid chromatograph, among liquid chromatographs, and performing separation/fractionation, and then performing concentration is used.

With respect to concentration, although a vacuum evaporator is also used, concentration by a trap column is used often because, if an elimination column is used in combination, additives and the like may be eliminated (see Patent Document 1).

Generally, in the case of trapping a sample in a trap column, if the sample concentration is high, or the solvent strength of a sample solvent is high, trapping is difficult, and thus, a diluted sample is delivered to the trap column so as to facilitate trapping.

Dilution may be performed at the time of adjusting the sample, but in the case where the sample volume after dilution is excessively high, processing is difficult, and thus, dilution is performed online. In online dilution, a flow path similar to the flow path structure of a sample concentration device as shown in FIGS. 1 and 4 is used as an embodiment.

In FIG. 1, a high-pressure valve 2 is switched to an injection position according to which a sample loop 4 is incorporated in a main flow path including a sample push unit 5 and a trap column 8, and in FIG. 4, the high-pressure valve 2 is switched to a metering position according to which the sample loop 4 is incorporated to a metering flow path including a syringe pump 3 and a sampling needle 30.

According to such a sample concentration device, the high-pressure valve 2 is switched from an idling state (the high-pressure valve 2 is in the state in FIG. 1, which is the same as the injection position) to a sample metering state in FIG. 4, and a sample is drawn by the syringe pump 3 at an autosampler 1 and is introduced into the sample loop 4. Next, the high-pressure valve 2 is switched to the injection state in FIG. 1, and the sample in the sample loop 4 is pushed out from the sample loop 4 by a mobile phase delivered from the sample push unit 5. Then, the sample is diluted by being mixed with a diluent (normally, of the same composition as the mobile phase) delivered from the make-up unit 6 at the three-way joint 7 on the main flow path, and is lead to, and trapped in, the trap column 8.

The dilution rate at this time is normally several times the sample volume. The make-up unit 6 is expected to compensate for the flow rate of (dilution rate−1) times the flow rate of the sample push unit 5 at least until the sample passes through the three-way joint 7. After the sample passes through the three-way joint 7, the sample push unit 5 is expected to perform delivery until the sample is completely fixed to the trap column 8.

Since separation/analysis are not performed by the sample concentration device, normally, a mobile phase does not have to be delivered from the sample push unit 5 at the time of idling, and the make-up unit 6 does not have to perform delivery either. Especially, in the case of performing concentration of a large volume of sample by a large volume of mobile phase and a large volume of diluent, it is desirable to start delivery immediately before concentration is performed, and to immediately stop delivery when concentration is complete. However, in reality, it is not easy to control the delivery operation in this manner due to the following circumstances.

An example of a sample that is used by such a sample concentration device is a single component sample obtained by separating synthesized compounds by a preparative system. As an example, the fractionation for two component peaks according to the preparative system are shown in FIG. 3. In this example, the peak of a component B (retention time: 5.8 min) overlaps a tailing component A (retention time: 5.7 min). When a flow rate of 100 mL/min and a maximum fraction volume of 10 mL for one fraction vial are given as conditions, the upper limit of the volume of the vial is reached in 0.1 minutes. Then, in this example, it can be seen that when a fraction 9 reaches the maximum fraction volume 10 mL of a vial #1, it is switched to a fraction 10, and then, before the maximum fraction volume 10 mL of a vial #2 is reached, the rise of a peak of the component B is detected and switching to a fraction 11 is performed, and switching to a fraction 12 takes place when a fall of the peak of the component B is detected.

In the example in FIG. 3, the fractions 9, 10 and 12, which are a single component, are taken as a sample, and are injected to a concentration system based on a trap column, and concentration is performed.

With a general liquid chromatography analysis system, sample injection and the analysis process are programmed according to a table called a batch table (referred to also as a sequence table or a sample set). One row of the batch table corresponds to one analysis, and each row contains the position of a sample vial, the sample volume, and other analysis conditions.

Other analysis conditions include an analysis initial parameter set, a pre-injection processing program for customizing the operation of the autosampler 1 (normally referred to as a pre-treatment program. In the case of not performing customization, a standard pre-treatment operation is internally programmed), a time program (also referred to as an event or an event program), and the like, and normally, these are stored in a parameter set called an instrument method. (The pre-treatment program may be specified in the batch table independently of the instrument method.)

The process in one row of the batch table is performed in the order of downloading of the position of a sample vial, the sample volume and other analysis conditions to the device (download), execution of the pre-treatment program (pre-treatment execution), and execution of a time program and start of recording of a chromatogram (analysis execution).

As programming methods of the example in FIG. 3, there are the following (a) to (d).

(a) The fractions 9, 10 and 12 are transferred to one vial and are taken as one sample, and programming is performed with "one row/one injection".

The "injection" here refers to connection of the sample loop 4 to the main flow path by switching of the high-pressure valve 2 to the injection position after one sample is introduced into the sample loop 4 by the pre-treatment program. In many cases, an event signal (an electrical signal, a communication command, a software instruction) for performing recording start of a chromatogram or a time program is output simultaneously with the switching of the high-pressure valve 2, but the event signal may be output before or after the switching of the high-pressure valve 2.

In this case, according to the instrument method, an "injection" process for one sample is performed by the pre-treatment program, and the sample push unit 5 and the make-up unit 6 are controlled by the time program, and fixation of the sample to the trap column 8 is performed. Here, after the sample is introduced into the sample loop 4, and before the high-pressure valve 2 is switched, an event signal is output to start delivery of a mobile phase and a diluent by the sample push unit 5 and the make-up unit 6 by the time program, and switching of the high-pressure valve 2 is performed after the delivery becomes stable.

(b) Programming is performed assuming "three rows/two loadings, one injection" for the fractions 9, 10 and 12.

The "loading" here means that the high-pressure valve 2 is not switched after a sample is introduced into the sample loop 4 by the pre-treatment program. In the case of this example, one row corresponds to one loading, and thus, after the "loading", an event signal is output by the pre-treatment program and the time program is started, but since the sample push unit 5 and the make-up unit 6 do not have to operate, the time program is ended swiftly. Additionally, since the time program is ended swiftly, the autosampler 1, which cannot output an event signal unless the high-pressure valve 2 is switched, may perform a process corresponding to the "loading" in the "injection" process, but detailed description here is omitted.

In reality, an instrument method for sample push for until the N−1th row and an instrument method for injection for the Nth row are prepared and combined. In the case of this example, "loading" of one sample is performed by the pre-treatment program by the instrument method for sample push for the fractions 9 and 10, and "injection" of one sample and fixation of the sample to the trap column 8 are performed by the pre-treatment program by the instrument method for injection for the fraction 12. The contents of the processing by the instrument method for injection are the same as the contents of the processing by the instrument method of (a). Here, the samples of the fractions 9 and 10 are sent to the trap column 8 together with the sample of the fraction 12.

(c) Programming is performed assuming "one row/two loadings" for the fraction 9 with fixed volume and the fraction 10 with variable volume, and assuming "one row/one injection" for the fraction 12 with variable volume.

In reality, an instrument method for sample push of "one row/N loading (N: 1 or more, N−1 fraction: fixed volume, one fraction: variable volume)" and an instrument method for injection of "one row/one injection" are prepared and combined. In the case of this example, "loading" of one sample with fixed volume and one sample with variable volume (the volume is specified in the batch table) is performed by the pre-treatment program by the instrument method for sample push for the fractions 9 and 10, and "injection" of one sample with variable volume (the volume is specified in the batch table) and fixation of the sample to the trap column 8 are performed by the pre-treatment program by the instrument method for injection for the fraction 12. The contents of the processing by the instrument method for injection are the same as the contents of the processing by the instrument method of (a).

(d) Programming is performed assuming "one row/two loadings, one injection" for the fractions 9, 10 and 12, and "loading" and "injection" are performed by the pre-treatment program of the autosampler included in the instrument method by separately customizing the volumes of the fraction 9, 10 and 12.

According to this method, the instrument method performs, by the pre-treatment program, "loading" of each of the samples of the fractions 9 and 10, and "injection" of the sample of the fraction 12, and performs fixation to the trap column 8. The contents of the processing after introduction into the sample loop 4 are the same as the contents of the processing by the instrument method of (a).

In any of (a) to (d), the make-up unit 6 has to deliver a diluent by the volume several times the actual sample injection volume.

Here, the "actual sample injection volume" that is introduced into the sample loop 4 and injected into the main flow path is the total sample volume in the case where no special pre-treatment is required, and is the volume obtained by adding the volume of an additive to the total sample volume in the case where pre-treatment such as mixing of an additive is to be performed, and specification thereof in advance is difficult. Accordingly, instead of the "actual sample injection volume", normally, the "maximum sample injection volume" is defined based on the volume of the sample loop 4 and the number of times of injection into the main flow path, and the maximum fraction volume and the maximum number of fraction vials.

The main objects of a liquid chromatography analysis are separation and analysis, and the retention time of a sample is not dependent on the sample volume, and only the tailing factor determining the elution range of the sample is dependent on the sample volume. Accordingly, in the case of using a specific sample, the analysis time at the liquid chromatography analysis may be assumed to be constant without depending on the sample volume.

Additionally, the tailing factor in separation/analysis is an index defined as $W_{0.05}/2f$, and the greater tailing factor means greater tailing. Here, $W_{0.05}$ is the peak width at the height which is 5% of the peak height, and f is the distance, within $W_{0.05}$, from the rise of the peak to the top of the peak.

With the device control of a liquid chromatography analysis device, an operation may be programmed in the instrument method based on the analysis time and the time program (referred to also as an event or an event program), but control of operating a solvent delivery pump based on the actual sample injection volume cannot be performed.

Accordingly, with the liquid chromatography analysis device, in the case of performing trap concentration, a method of controlling the pump by switching the instrument method prepared for each sample volume range, or a method of controlling the pump by a time calculated with respect to the maximum sample injection volume is used.

PRIOR ART DOCUMENTS

Patent Documents

Patent Document 1: Japanese Patent No. 3476417

SUMMARY OF THE INVENTION

Problem to be Solved by the Invention

In theory, in any of the programming methods (a) to (d), the volume of every fraction may fall below the maximum fraction volume due to superimposition of an interfering component. In a conventional technique, in the case where the actual sample injection volume is one-tenth of the maximum sample injection volume, there is wasteful consumption of solvents of (maximum sample injection volume)×9/10 for a mobile phase, and (maximum sample injection volume)×(dilution rate−1)×9/10 for a diluent, and more time is also wastefully consumed as the amount of solvent consumption is increased.

If the maximum sample injection volume is 50 mL, the dilution rate is 5 times, and there is no mixing of additives, delivery of 250 mL of solvent (mobile phase+diluent) becomes necessary per sample, and of this, 225 mL of solvent will be wastefully consumed.

To deliver 250 mL of solvent per sample means that 25 L of solvent becomes necessary for 100 samples, and when considering the burden of preparation and replenishment of solvent and the environmental burden of solvent, in addition to the purchase cost of solvent itself, there is a demand from users to suppress the amount of solvent consumption as much as possible.

To minimize the amount of solvent consumption, a method of dividing the sample volume range, specifying the maximum sample volume and defining the instrument method for each range, and using the instrument method accordingly is used in many cases, but this method requires development and maintenance of many instrument methods.

Furthermore, the fraction volume and the number of fractions of a sample to be concentrated by the trap column depend greatly on the density of the sample, the retention time, and the degree of separation from other components, and cannot be decided unconditionally. The reasons are as follows.

The following can be said with respect to the peak width of a chromatogram.

(A) The peak width of a single component tends to be wider as the density is higher in the case of the same mobile phase composition and delivery flow rate.

(B) With respect to peak widths of a plurality of components, the peak width tends to be wider for the component with a long retention time in the case of the same mobile phase composition and delivery flow rate and the same density.

(C) The retention time tends to be shorter as the delivery flow rate is greater in the case of the same mobile phase composition.

(D) The retention time may be changed by changing the mobile phase composition in the case of the same delivery flow rate.

Accordingly, the number of fractions of a single component peak is different depending on the conditions of delivery. The number of fractions of a single component peak is also different depending on the sample. The fraction volume and the number of fractions of multiple component peaks except the interfering component peak are also different depending on the sample. This is because the peak widths and the degree of overlapping of peaks are different depending on the sample.

As a problem unique to the programming method (a), there is the possibility of the vial volume being exceeded when several fractions are assembled.

As a problem unique to the programming method (b), there is a need for a mechanism for handling a sample volume of a plurality of fractions.

As a problem unique to the programming method (c), there is a need to prepare the instrument methods for the number of fractions. In the case where there is a great variation in the sample volume, it is difficult for a user to select an appropriate instrument method according to the sample volume.

As a problem unique to the programming method (d), there is a need for a task of rewriting the sample position and the volume for each sample by the pre-treatment program, and in the case where there is a great number of samples, adopting this method is not realistic.

The sample concentration methods described above are only examples, and description of the method of specifying the fraction volume and the number of fractions of a sample to be concentrated by the trap column, and the method of specifying the actual sample injection volume is omitted in the present specification; the present invention is not limited to such concentration methods, and has its object to enable reduction in the amount of solvent consumption by performing control of a solvent delivery pump according to the actual sample injection volume without preparing a plurality of instrument methods.

Means for Solving Problem

A sample concentration device of the present invention includes an autosampler for injecting a certain volume of sample, a trap column, a sample push unit for delivering a sample injected by the autosampler to the trap column by a solvent delivery pump for sample push, a make-up unit for compensating for a diluent by a solvent delivery pump for make-up with respect to a sample pushed out by the sample push unit, and a controller for controlling operations of the autosampler, the sample push unit, and the make-up unit.

Also, the controller includes a pump stop timing setting unit for setting a first timing T1 of completion of dilution of a sample, and a subsequent second timing T2 of completion of trapping of a sample in the trap column, a dilution control unit for causing the solvent delivery pump for make-up of the make-up unit to operate, and for stopping operation of the solvent delivery pump for make-up at the first timing T1 set by the pump stop timing setting unit, and a sample push control unit for causing the solvent delivery pump for sample push of the sample push unit to operate, and for stopping operation of the solvent delivery pump for sample push at the second timing T2 set by the pump stop timing setting unit.

The first timing T1 of completion of dilution of a sample is the timing at which the end of a sample bulk passes through a three-way joint and at which all of the end of a tailing portion of the sample bulk remained on the inner surface of a pipe passes through the three-way joint, and the second timing T2 of completion of trapping of a sample in the trap column is the timing at which the end of the tailing portion of the sample bulk passes from the three-way joint through the inside of the trap column.

In a first mode, the pump stop timing setting unit sets a timing calculated based on a sample injection volume as the timing T1, and sets a timing calculated based on a sample sweep volume as the timing T2. The "sample sweep volume" here is the volume necessary for the end of a tailing portion of a sample bulk to pass from the three-way joint through the inside of the trap column and for the sample to be fixed to the trap column, and is mainly dependent on the volume of the trap column.

In this case, an example of the pump stop timing setting unit stores in advance a timing T1 calculated based on a maximum sample injection volume and a timing T2 calculated based on a sample sweep volume, and when notified of a sample injection volume by the autosampler, calculates a timing T1 based on the notified sample injection volume and takes the timing T1 as a set value of the timing T1, and when not notified of a sample injection volume by the autosampler, takes the timing T1 stored in advance as a set value.

A second mode includes a probe for detecting a sample bulk end at a stage preceding the trap column, and in this case, the pump stop timing setting unit sets a timing calculated based on a timing of a detection signal of the probe as the timing T1, and sets a timing calculated based on a sample sweep volume as the timing T2.

In the second mode, even when addition or mixing of an additive, dilution or the like is performed for a sample by the pre-treatment program, the controller may directly detect the end of a sample bulk injected into a flow path, and there is no need to correct the sample injection volume input by the autosampler.

In a preferred mode, the controller swiftly stops a time program and ends a concentration operation after stopping operation of the solvent delivery pump for sample push at the second timing T2. Accordingly, the sample concentration device swiftly ends a sample concentration process after delivery of a solvent is stopped, and the execution time at the time of system operation may be greatly reduced.

Effect of the Invention

With the sample concentration device of the present invention, since the solvent delivery pump for sample push is stopped at the time of completion of trapping of a sample in the trap column, and the solvent delivery pump for make-up is already stopped by this time, only the minimum required solvent for trapping the sample is consumed, and the amount of solvent consumption at the time of system operation may be greatly reduced.

Also, there is no need to prepare a plurality of instrument methods for controlling the solvent delivery pump for sample push and the solvent delivery pump for make-up according to the range of sample injection volume, and development and maintenance of instrument method are facilitated.

BRIEF DESCRIPTION OF DRAWING

FIG. 7 is a time chart showing an operation of the present embodiment.

MODE FOR CARRYING OUT THE INVENTION

Embodiment 1

Figure 1:
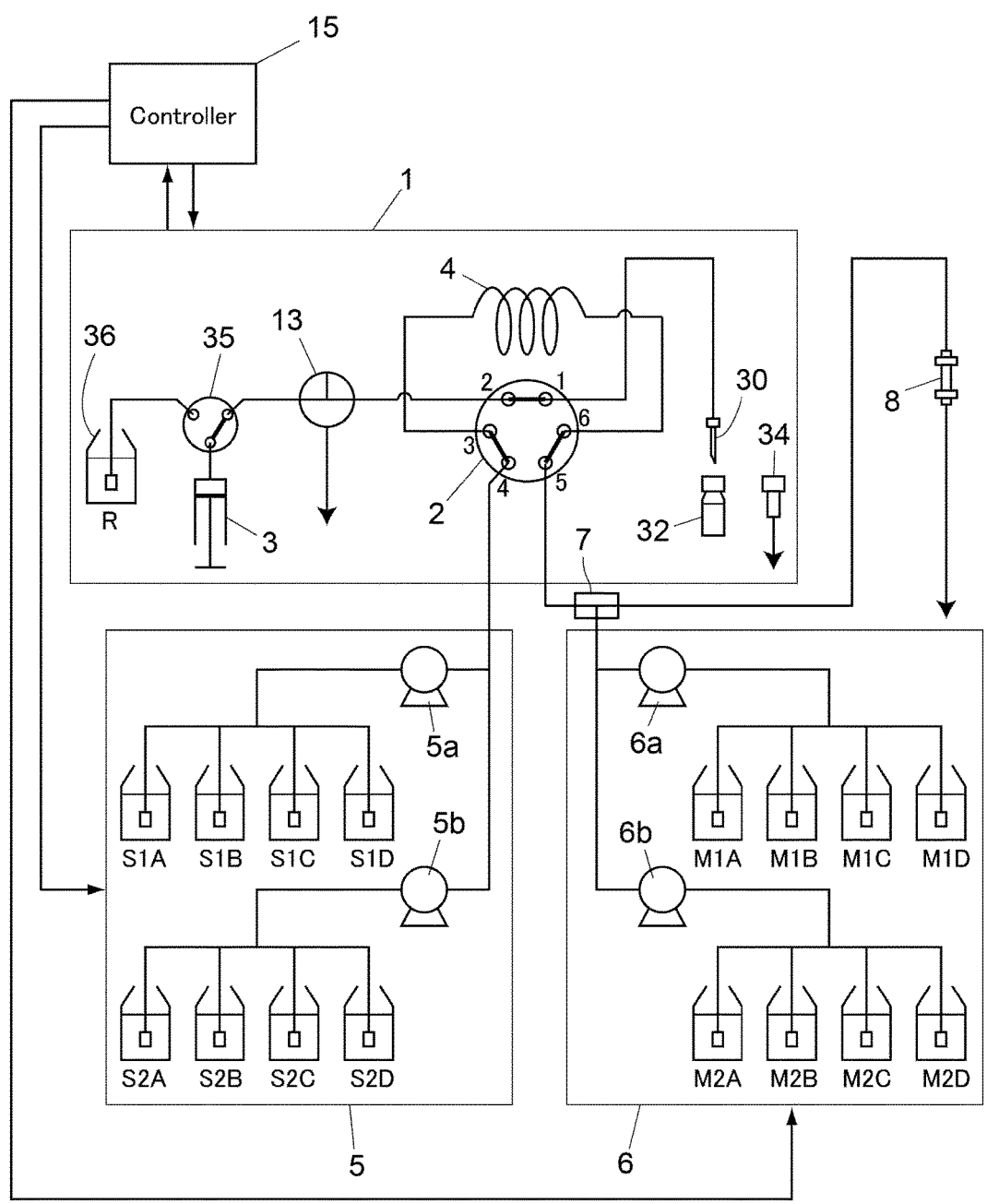
FIG. 1 is a schematic flow path diagram showing a first embodiment in a flow path state at the time of idling or a flow path state at the time of injection/sample trapping.
Figure 4:
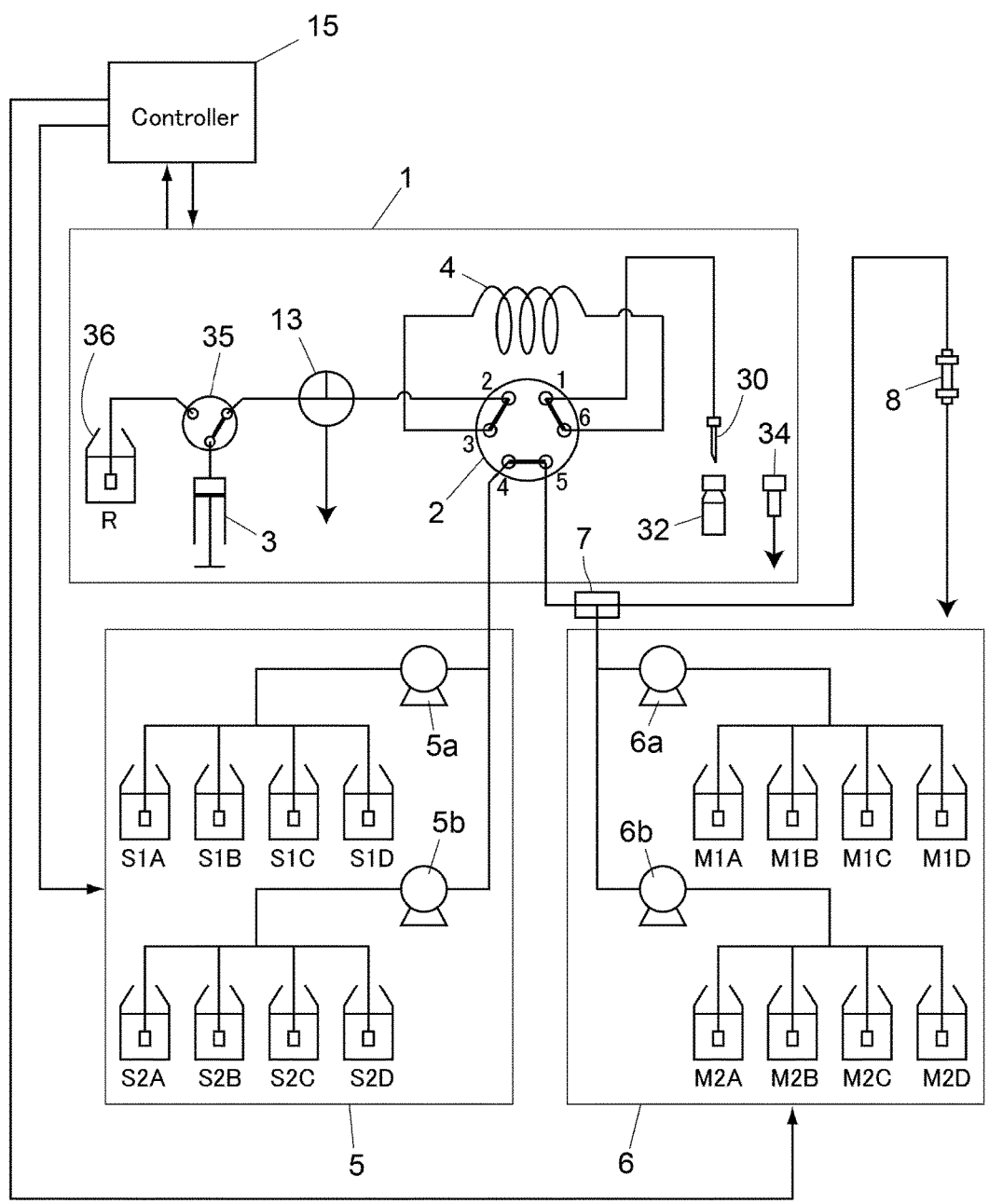
FIG. 4 is a schematic flow path diagram showing the present embodiment in a flow path state at the time of sample metering.

FIGS. 1 and 4 schematically show a sample concentration device of a first embodiment. The sample concentration device is a device for injecting a sample, and trapping (collecting) the sample in a trap column, and includes an autosampler 1 for injecting a certain volume of sample, a trap column 8, a sample push unit 5 for delivering a sample injected by the autosampler 1 to the trap column 8 by a solvent delivery pump 5a or 5b for sample push, a make-up unit 6 for compensating for a diluent by a solvent delivery pump 6a or 6b for make-up with respect to a sample pushed out by the sample push unit 5, and a controller 15 for controlling operations of the autosampler 1, the sample push unit 5, and the make-up unit 6.

The sample concentration device is sometimes incorporated in a liquid chromatograph as a part of the liquid chromatograph. In such a case, the trap column 8 is separated from a concentration device and is connected to an analysis system by a flow path switching valve, and a sample trapped in the trap column 8 is eluted by a solvent delivery pump for elution, and is analyzed in the column. The sample concentration device of the present invention also includes such a mode, but in the embodiments, description of parts other than the concentration device is omitted.

At the autosampler 1, a sample loop 4 is connected between two ports of a high-pressure valve 2, and a sampling needle 30 is connected to another port of the high-pressure valve 2, and a syringe pump 3, which is a metering pump, is connected to further another port of the high-pressure valve 2. The sample push unit 5 is connected to further another port of the high-pressure valve 2, and the trap column 8 is connected to further another port of the high-pressure valve 2.

At the autosampler 1, a sample in a sample vial 32 is drawn by the syringe pump 3 from the sampling needle 30 into the sample loop 4 (FIG. 4), and the high-pressure valve 2 is switched, and thus, the sample drawn into the sample loop 4 is delivered to the trap column 8 by a solvent from the sample push unit 5 (FIG. 1).

At the autosampler 1, a drain valve 13 is connected between the syringe pump 3 and the high-pressure valve 2. After an injection process, a mobile phase that is drawn into a metering flow path of the syringe pump 3 from the sample loop 4 at the time of drawing of the sample is discharged from the drain valve 13.

At the autosampler 1, a rinsing port 34 for rinsing the sampling needle 30 is arranged, and a rinsing liquid 36 is connected to the syringe pump 3 via a switching valve 35. At the time of rinsing of the sampling needle 30 and the flow path from the high-pressure valve 2 to the sampling needle 30 in the injection state in FIG. 1, rinsing is performed by inserting the sampling needle 30 into the rinsing port 34 and drawing the rinsing liquid into the syringe pump 3 via the switching valve 35, and then, switching the switching valve 35, and discharging the rinsing liquid which was drawn into the syringe pump 3 from the sampling needle 30.

The flow path structure (the connection method of the high-pressure valve 2, the sample loop 4, and the sampling needle 30) of the autosampler 1 may take another structure. For example, a structure is possible where the syringe pump 3 on a separate flow path is directly connected to the sampling needle 30, an injection port is connected to another port of the high-pressure valve 2, and a sample is pushed into the sample loop 4. Also, for example, a structure is possible where the sample loop 4 is connected to one port of the high-pressure valve 2 and the sampling needle 30 is directly connected at its tip end, where the syringe pump 3 on a separate flow path is connected to the sampling needle 30, and where an injection port is connected to another port of the high-pressure valve 2, and after a sample is drawn into the sample loop 4 from the sampling needle 30 by the syringe pump 3, the sampling needle 30 is inserted into the injection port and the total volume of the sample in the sample loop 4 is injected into the flow path (total volume injection method).

Two solvent delivery pumps 5a and 5b for sample push are provided to the sample push unit 5, and since these solvent delivery pumps 5a and 5b are connected to the high-pressure valve 2 in parallel, one of two types of solvents or a mixture thereof may be supplied. However, the sample push unit 5 may alternatively be provided with only one solvent delivery pump.

Four types of solvents may be drawn into each of the solvent delivery pumps 5a and 5b, but the number of solvents is not limited thereto, and any number of types may be used including one type.

A three-way joint 7 is provided on the flow path through which a sample is transferred from the high-pressure valve 2 to the trap column 8, and the make-up unit 6 is connected via the three-way joint 7. The make-up unit 6 is for compensating for a diluent to dilute a sample.

Two solvent delivery pumps 6a and 6b are also provided to the make-up unit 6, and since these solvent delivery pumps 6a and 6b are connected to the high-pressure valve 2 in parallel, one of two types of solvents or a mixture thereof may be supplied as a diluent. However, the make-up unit 6 may alternatively be provided with only one solvent delivery pump. Four types of solvents may be drawn into each of the solvent delivery pumps 6a and 6b, but the number of solvents is not limited thereto, and any number of types may be used including one type.

The controller 15 may be realized by a dedicated computer of the concentration device or of a liquid chromatograph in which the concentration device is installed, or may be realized by a general-purpose personal computer. Moreover, it may be realized by both the dedicated computer and the personal computer.

The autosampler 1, the sample push unit 5, the make-up unit 6, and the controller 15 may be integrated, or they may be separate units.

Figure 2:
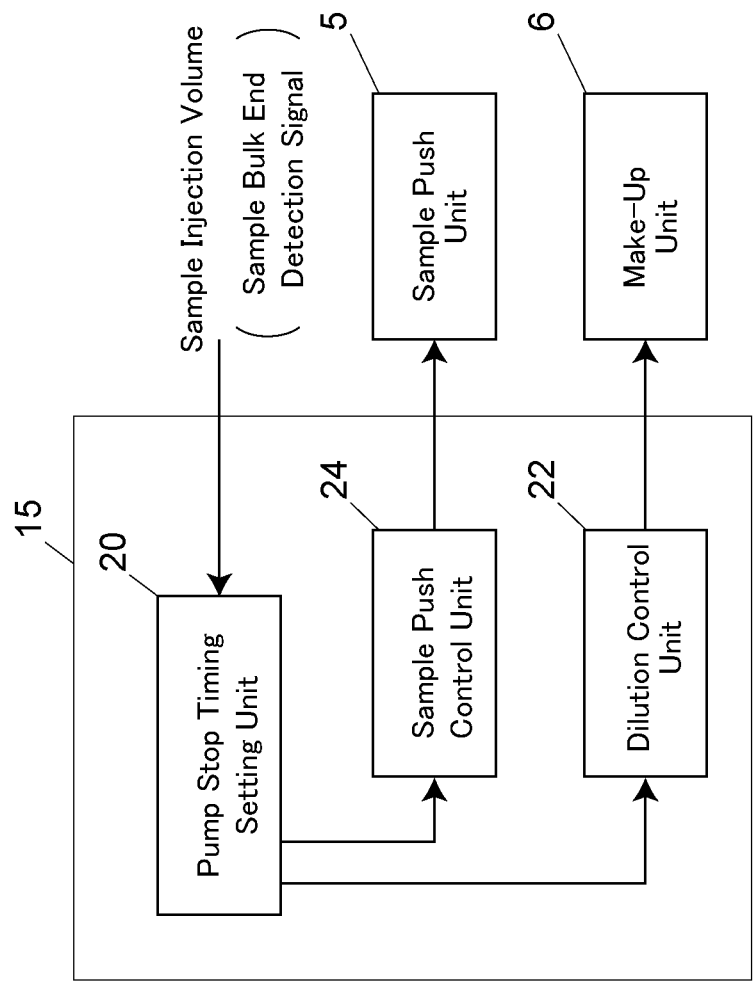
FIG. 2 is a block diagram for describing functions of a controller of a sample concentration device of the present invention.
Figure 3:
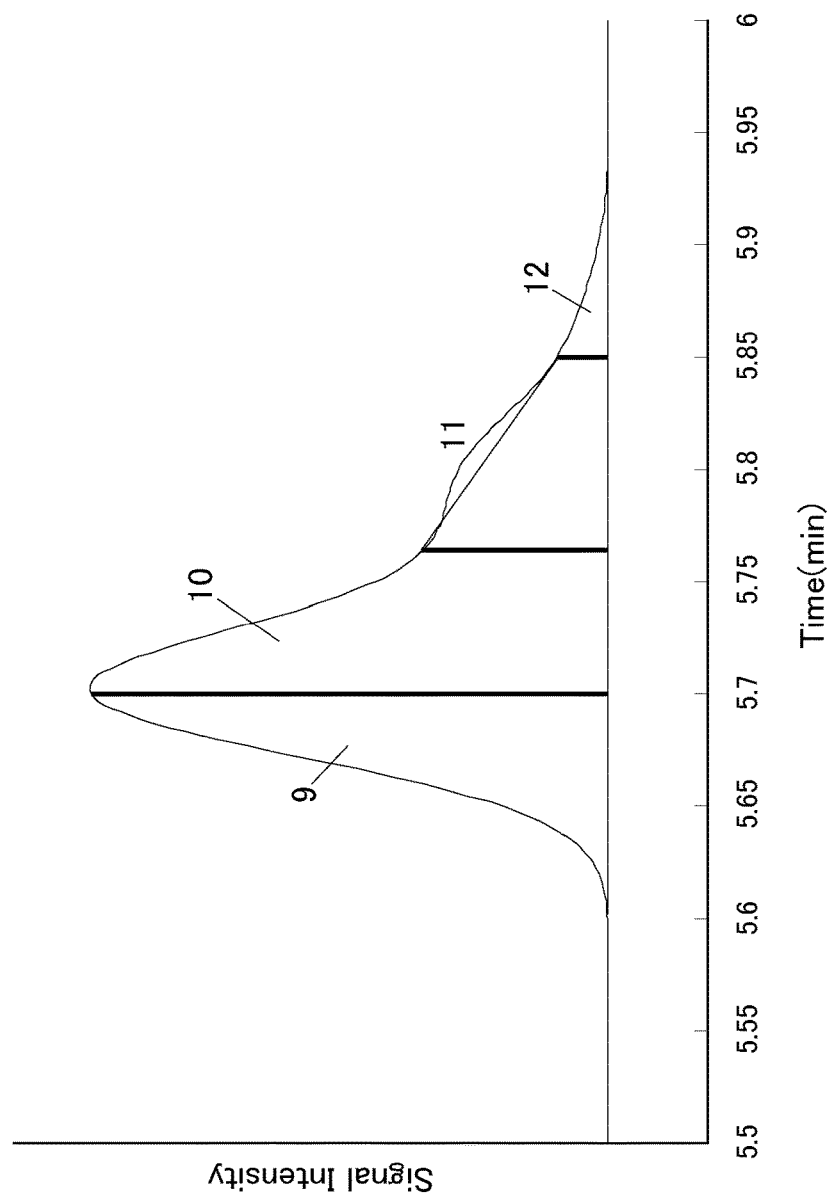
FIG. 3 is a waveform diagram showing example fractionation of two component peaks by a preparative system for obtaining a sample for the sample concentration device.

The functions of the controller 15 are the structures shown in FIG. 2. A pump stop timing setting unit 20 sets a first timing T1 of completion of dilution of a sample, and a subsequent second timing T2 of completion of trapping of a sample in the trap column 8. A dilution control unit 22 causes the solvent delivery pumps 6a and 6b of the make-up unit 6 to operate, and stops the operations of the solvent delivery pumps 6a and 6b at the first timing T1 set by the pump stop timing setting unit 20. A sample push control unit 24 causes the solvent delivery pumps 5a and 5b of the sample push unit 5 to operate, and stops the operations of the solvent delivery pumps 5a and 5b at the second timing T2 set by the pump stop timing setting unit 20.

In this embodiment, the pump stop timing setting unit 20 sets the timing T1 based on the sample injection volume. Specific description will be given later, but as an example, the pump stop timing setting unit 20 stores in advance a timing T1 calculated based on the maximum sample injection volume, and when notified of a sample injection volume by the autosampler 1, calculates a timing T1 based on the notified sample injection volume and takes the timing T1 as the set value of the timing T1, and when not notified of a sample injection volume by the autosampler 1, takes the timing T1 stored in advance as the set value.

FIG. 1 shows the state of the high-pressure valve 2 at the time of idling and at the time of sample trapping. At the time of sample metering, the high-pressure valve 2 is rotated to be in the state in FIG. 4.

Figure 5:
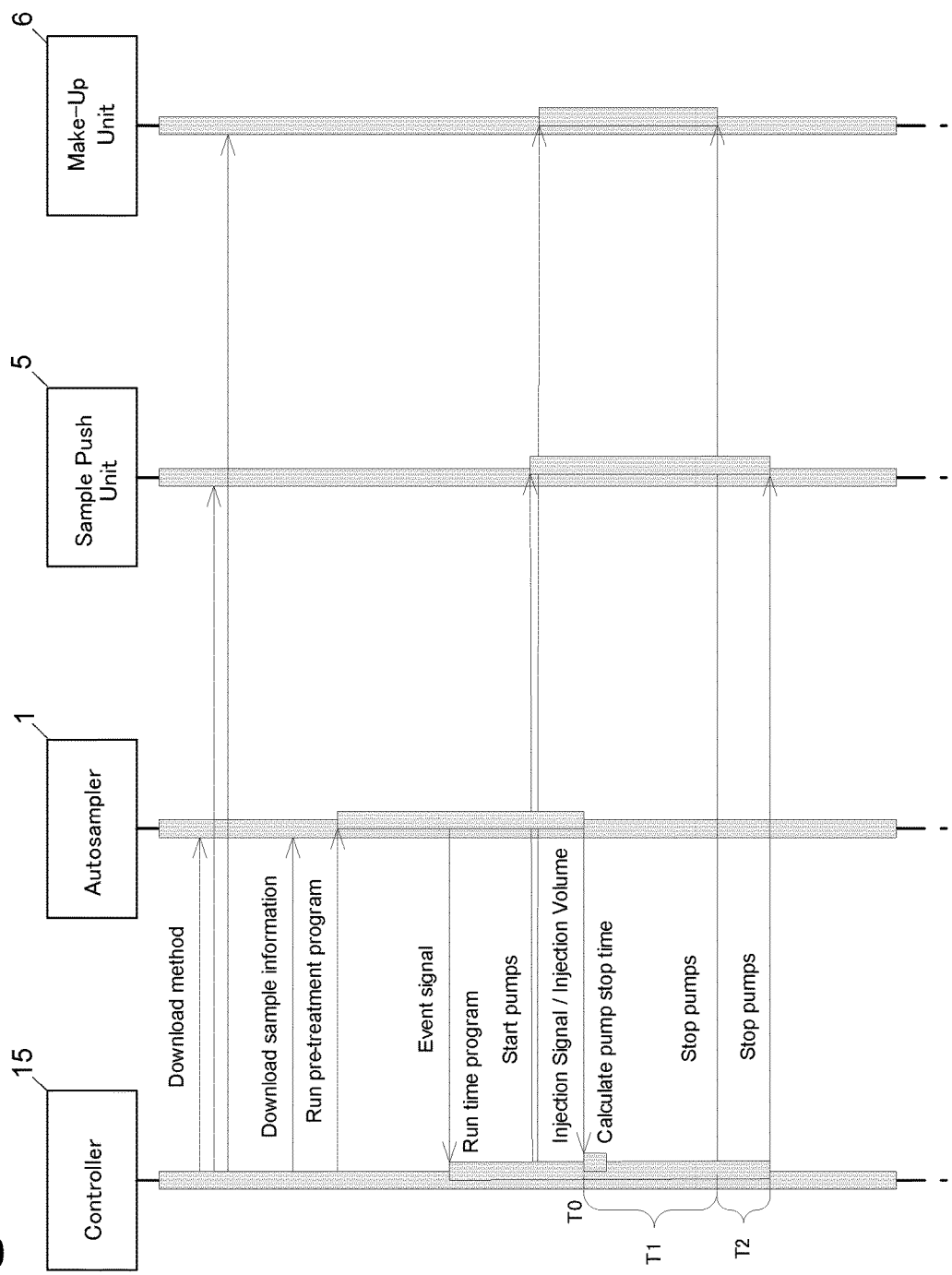
FIG. 5 is a time chart showing an operation of the present embodiment.

A control method according to the present embodiment for performing sample concentration will be described with reference to the time chart in FIG. 5.

First, an instrument method for controlling the sample concentration device is downloaded from the controller 15 to the autosampler 1, the sample push unit 5, the make-up unit 6, and other necessary units (Download method).

The instrument method includes, in addition to parameters for controlling the autosampler 1, the sample push unit 5, and the make-up unit 6, a time program, a pre-treatment program, and the like.

The time program and the pre-treatment program may be executed by the controller 15, or by each of the autosampler 1, the sample push unit 5, and the make-up unit 6.

One of the parameters for controlling the sample push unit 5 and the make-up unit 6 is the dilution rate. The dilution rate is normally determined based on the flow rate ratio of the sample push unit 5 and the make-up unit 6.

As other parameters for controlling the sample push unit 5 and the make-up unit 6, there are the first timing T1 and the second timing T2 that are set by the pump stop timing setting unit 20. The first timing T1 is the timing of stopping the operations of the solvent delivery pumps 6a and 6b for make-up. To determine this first timing T1 according to the sample injection volume, the sample injection volume is multiplied by, for example, a factor such as the tailing factor of a sample bulk.

The second timing T2 is the timing of stopping the operations of the solvent delivery pumps 5a and 5b for sample push. To determine this second timing T2, for example, a sample sweep volume (the volume necessary for fixation of a sample) that is dependent mainly on the volume of the trap column 8 is taken into account.

The pre-treatment program is a program including sequential executable commands included in the instrument method, and includes as necessary, in addition to operations such as addition/mixing of an additive or dilution at the sample vial 32, discharging of a mobile phase in the metering flow path of the syringe pump 3 after injection, and rinsing of the sampling needle 30 and the flow path from the high-pressure valve 2 to the sampling needle 30, an operation of rewriting the sample position for drawing a sample at the autosampler 1 and the volume to be drawn that are normally specified in a batch table.

The time program is a program for determining the timings (analysis elapsed time of command execution) of controlling the operations of the autosampler 1, the sample push unit 5, the make-up unit 6, and other necessary units after output of a start signal (after an analysis is started), and includes the timings of controlling the operations of the sample push unit 5 and the make-up unit 6 using parameters T1 and T2.

Next, the controller 15 downloads, to the autosampler 1, sample information such as the position of the vial (sample vial) of a sample, the injection volume, and the like (Download sample information).

Then, the controller 15 instructs the autosampler 1 to start the pre-treatment program (Run pre-treatment program).

According to the contents of the pre-treatment program, the autosampler 1 switches the high-pressure valve 2 to the sample metering position (the state in FIG. 4), and starts a sample drawing operation.

After the sample drawing operation, the autosampler 1 transmits to the controller 15, according to the contents of the pre-treatment program, an event signal for starting the time program (Event signal), and the controller 15 starts the time program (Run time program). The event signal may be a digital signal generated by software, or may be an analog signal such as a relay signal.

The controller 15 receives the event signal, and causes the sample push unit 5, the make-up unit 6, and other necessary units to perform an analysis operation including execution of the time program (Start pumps).

This is taken as the start time of the time program.

According to the contents of the pre-treatment program, at the time of switching the high-pressure valve 2 to the injection position (the state in FIG. 1), the autosampler 1 notifies the controller 15 of an injection start signal and the sample injection volume (Injection Signal/Injection Volume). This is taken as a timing T0.

The controller 15 calculates the parameter T1 for stopping the make-up unit 6 with respect to the injection volume which has been notified.

The parameters T1 and T2 to be calculated are, for example, as follows.

The injection start notification time is taken as T0. The elapsed time (T0+T1) of the time program for stopping the solvent delivery pump of the make-up unit 6 is $$(T0+T1)=T0+V+\times Ft/M \quad (1),$$

where

V: sample injection volume which has been notified,

Ft: tailing factor,

M: flow rate of sample push unit 5.

The elapsed time (T0+T1+T2) of the time program for stopping the solvent delivery pump of the sample push unit 5 is $$(T0+T1+T2)=T0+T1+Vs/M \quad (2),$$

where

Vs: sample sweep volume.

Then, according to the calculated parameters T1 and T2, the controller 15 stops the make-up unit 6 when, after injection, dilution becomes unnecessary, and then, stops the sample push unit 5 after the sample is fixed to the trap column 8.

As an example, the make-up unit 6 is stopped after the lapse of time T0 (the time of sample injection) from the output of an event signal (start of the time program) and also after the lapse of time T1, and then the sample push unit 5 is stopped after the lapse of time T2.

In the embodiment, T1 that is calculated by using the maximum sample injection volume and T2 that is calculated by using the sample sweep volume are stored, and the time program is created based on the T1 and T2 that are stored. In the case where a sample injection volume is notified by the autosampler 1, and the value is not zero, operation is performed based on the T1 that is calculated by using the notified sample injection volume and the T2 that is calculated by using the sample sweep volume. In the case where the sample injection volume is not notified, or the value of the notified sample injection volume is zero, operation is performed based on the T1 that is calculated by using the maximum sample injection volume and the T2 that is calculated by using the sample sweep volume. This is because there may be an analysis operation where the autosampler 1 does not operate.

Additionally, the injection volume to be notified by the autosampler 1 may be the sample volume input by the controller 15, or in the case where addition/mixing of an additive or dilution is performed by the pre-treatment program, this may be taken into account with respect to the volume.

Furthermore, the controller 15 may use, as the sample volume, the sample volume input to the controller 15 as it is, instead of the injection volume notified by the autosampler 1, or may use an injection volume calculated based on the contents of the pre-treatment program or the parameters of the instrument method.

Additionally, the sample concentration device of this embodiment assumes delivery of a large volume, and thus is an embodiment according to which the time program is started in the pre-treatment program to start delivery by the solvent delivery pump, and then a sample is injected after the delivery becomes stable, but it is needless to say that sample injection may be swiftly performed by starting delivery during idling, before the pre-treatment program is started, starting the time program, in the pre-treatment program, at the same time as injection is enabled, and starting delivery by the solvent delivery pumps of the sample push unit 5 and the make-up unit 6.

Embodiment 2

Figure 6:
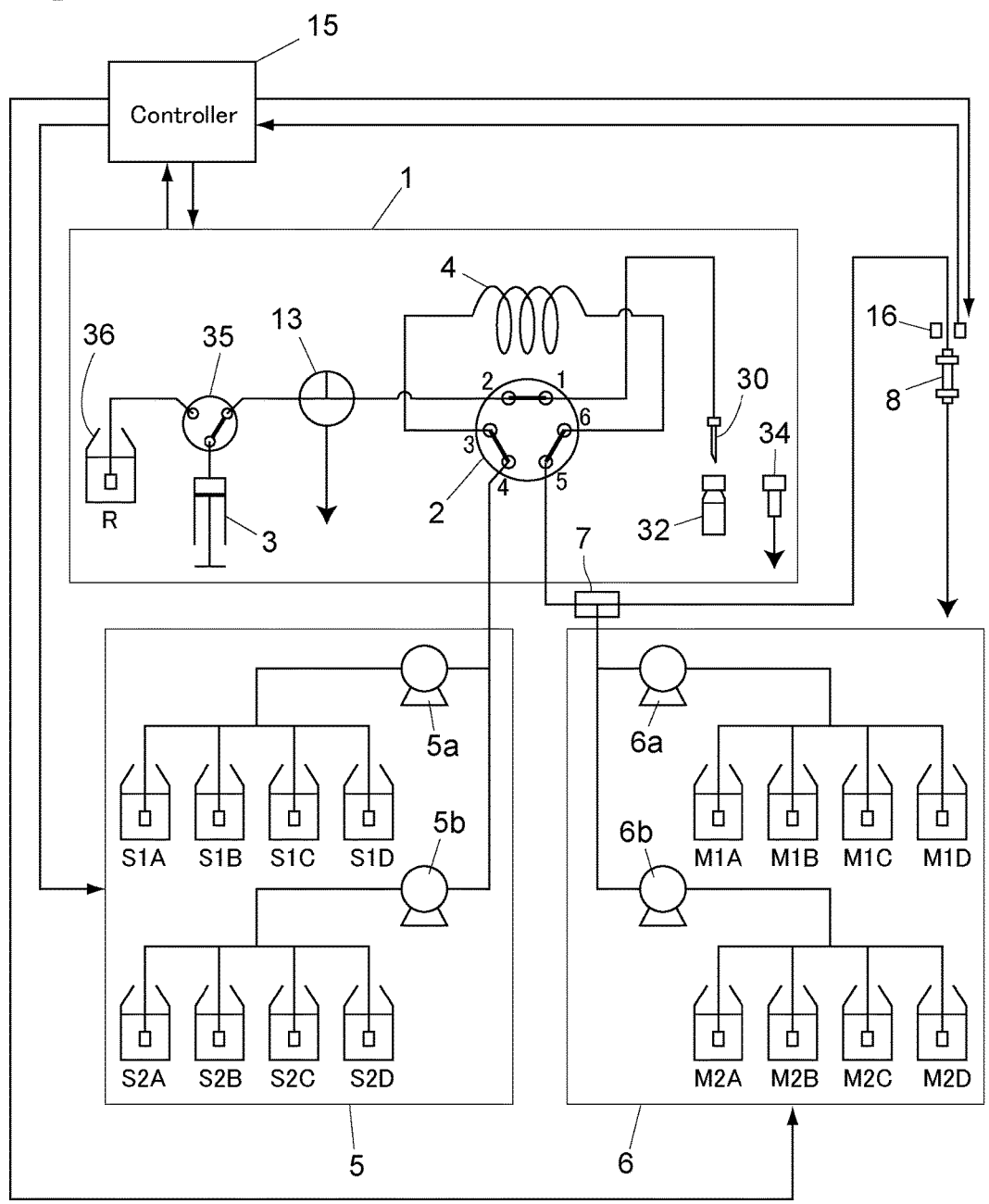
FIG. 6 is a schematic flow path diagram showing a second embodiment.

FIG. 6 schematically shows a sample concentration device of a second embodiment.

One aspect that is different from the first embodiment is that a sample end detection probe 16 is provided at a stage preceding the trap column 8, and the end of a sample that is introduced into the trap column 8 is detected. Another difference is that, since the sample end detection probe 16 is provided, the pump stop timing setting unit 20 at the controller 15 shown in FIG. 2 is configured to set the timing T1 based on the timing of the detection signal of the probe 16. Other aspects such as the flow path structure are the same as in the first embodiment, and detailed description of the same parts will be omitted.

The sample end detection probe 16, for example, detects a change in the physical property between a mobile phase and a sample solvent. As the physical property, an optical property such as a refractive index may be cited, and the sample end detection probe 16 in this case optically detects a change in such an optical property.

The controller 15 detects the end of a sample bulk by taking the output of the sample end detection probe 16 as an input.

As a parameter for controlling the make-up unit 6 according to sample end detection by the sample end detection probe 16, for example, a delay time from passing of the end of a sample bulk to passing of a tailing portion, a parameter for tuning the detection sensitivity for a change in the physical property between a mobile phase baseline and a sample solvent, and the like may be cited.

A control method according to the present embodiment for performing sample concentration will be described with reference to the time chart in FIG. 7. The difference to the sample concentration control method according to the first embodiment is that, in the present embodiment, control is performed based on a sample end detection event by the sample end detection probe 16 instead of the injection timing of the autosampler 1.

The controller 15 calculates the parameters for stopping the sample push unit 5 and the make-up unit 6 in response to a sample end detection event (Event signal) from the sample end detection probe 16.

The parameters to be calculated are, for example, as follows.

The sample end detection time is taken as T0. Time 0 indicates the start of the time program. Time (T0+T1) for stopping the solvent delivery pump of the make-up unit 6 is $$(T0+T1)=T0+\text{delay time} \qquad (3).$$

The "delay time" is a temporal margin for guaranteeing passing of the end of a sample bulk to passing of the tailing portion.

The time (T0+T1+T2) for stopping the solvent delivery pump of the sample push unit 5 is $$(T0+T1+T2)=T0+T1+Vs/M \qquad (2a),$$

and is, in form, the same as Equation (2). Here, as defined above, Vs is the sample sweep volume, and M is the flow rate of the sample push unit 5.

It is also possible to use, as the sample end detection probe 16, or as an alternative device of the sample end detection probe 16, an optical detector such as an UV (ultraviolet) detector.

Also in this embodiment, the controller 15 may be realized by a dedicated computer of the concentration device or of a liquid chromatograph in which the concentration device is installed, or may be realized by a general-purpose personal computer. Moreover, it may be realized by both the dedicated computer and the personal computer.

The autosampler 1, the sample push unit 5, the make-up unit 6, the controller 15, and the sample end detection probe 16 may be integrated, or they may be separate units.

Embodiment 3

Normally, the analysis time is a fixed time that is specified as a part of the analysis conditions, or that is specified as the end time of the time program. The analysis time includes a sample concentration time.

When it is not notified of a sample injection volume or a notified sample injection volume is zero, a sample concentration device of the third embodiment is terminated at the end time of the time program set in advance, and when it is notified of a sample injection volume, it is normally terminated at the same time as the sample push unit 5 is stopped. To this end, the controller 15 swiftly stops the time program and ends the concentration operation after stopping the operation of the solvent delivery pumps 5a and 5b for sample push at the second timing T2.

EXPLANATION OF REFERENCE LETTERS

1: Autosampler
2: High-pressure valve
3: Syringe pump
4: Sample loop
5: Sample push unit
6: Make-up unit
7: Three-way joint
8: Trap column
9: Fraction component for vial #1 (only component A)
10: Fraction component for vial #2 (only component A)
11: Fraction component for vial #3 (components A and B)
12: Fraction component for vial #4 (only component A)
13: Drain valve
15: Controller
16: Sample detection end probe
20: Pump stop timing setting unit
22: Dilution control unit
24: Sample push control unit
34: Rinsing port
35: Switching valve
36: Rinsing liquid

The invention claimed is:

1. A sample concentration device comprising:
an autosampler for injecting a certain volume of sample;
a trap column configured to trap the sample so that the sample is concentrated;
a sample push unit for delivering a sample injected by the autosampler to the trap column by a solvent delivery pump for sample push;
a make-up unit configured to send a diluent by a solvent delivery pump so that the diluent is merged to a sample pushed out by the sample push unit at a merging point provided upstream of the trap column; and
a controller configured to control operations of the autosampler, the sample push unit, and the make-up unit,
wherein the controller comprises
a pump stop timing setting unit for setting a first timing T1 of completion of dilution of a sample, and a subsequent second timing T2 of completion of trapping of a sample in the trap column,
a dilution control unit for causing the solvent delivery pump for make-up of the make-up unit to operate, and for stopping operation of the solvent delivery pump for make-up at the first timing T1 set by the pump stop timing setting unit, and
a sample push control unit for causing the solvent delivery pump for sample push of the sample push unit to operate, and for stopping operation of the solvent delivery pump for sample push at the second timing T2 set by the pump stop timing setting unit,
wherein the pump stop timing setting unit sets a timing calculated based on a sample sweep volume as the second timing T2, and
the sample sweep volume is the volume necessary for the end of a tailing portion of a sample bulk to pass from the merging point through the inside of the trap column and for the sample to be fixed to the trap column.

2. The sample concentration device according to claim 1, wherein the pump stop timing setting unit sets a timing calculated based on a sample injection volume as the timing T1.

3. The sample concentration device according to claim 2, wherein the controller is configured to swiftly stop a time program and end a concentration operation after stopping operation of the solvent delivery pump for sample push at the second timing T2.

4. The sample concentration device according to claim 1, wherein the pump stop timing setting unit stores in advance a timing T1 calculated based on a maximum sample injection volume and a timing T2 calculated based on the sample sweep volume, and when notified of a sample injection volume by the autosampler, calculates a timing T1 based on the notified sample injection volume and takes the timing T1 as a set value of the timing T1, and when not notified of a sample injection volume by the autosampler, takes the timing T1 stored in advance as a set value.

5. The sample concentration device according to claim 4, wherein the controller is configured to swiftly stop a time program and end a concentration operation after stopping operation of the solvent delivery pump for sample push at the second timing T2.

6. The sample concentration device according to claim 1, comprising
   a probe for detecting a sample bulk end at a stage preceding the trap column,
   wherein the pump stop timing setting unit sets a timing calculated based on a timing of a detection signal of the probe as the timing T1.

7. The sample concentration device according to claim 6, wherein the controller is configured to swiftly stop a time program and end a concentration operation after stopping operation of the solvent delivery pump for sample push at the second timing T2.

8. The sample concentration device according to claim 1, wherein the controller is configured to swiftly stop a time program and end a concentration operation after stopping operation of the solvent delivery pump for sample push at the second timing T2.

* * * * *